US009469886B2

(12) United States Patent
Yvon et al.

(10) Patent No.: US 9,469,886 B2
(45) Date of Patent: Oct. 18, 2016

(54) HYDROGEN SENSOR WITH ACTIVE LAYER AND METHOD OF MANUFACTURING HYDROGEN SENSORS

(75) Inventors: Klaus Yvon, Bernex (CH); Edmond Koller, Geneva (CH); Jean-Philippe Rapin, Esery (FR); Michael Stalder, Bienne (CH)

(73) Assignee: The Swatch Group Research and Development Ltd, Marin (CH)

( * ) Notice: Subject to any disclaimer, the term of this patent is extended or adjusted under 35 U.S.C. 154(b) by 255 days.

(21) Appl. No.: 14/131,488

(22) PCT Filed: Jun. 6, 2012

(86) PCT No.: PCT/EP2012/060755
§ 371 (c)(1),
(2), (4) Date: Jun. 4, 2014

(87) PCT Pub. No.: WO2013/010721
PCT Pub. Date: Jan. 24, 2013

(65) Prior Publication Data
US 2014/0294676 A1    Oct. 2, 2014

(30) Foreign Application Priority Data

Jul. 15, 2011   (CH) .................................. 1191/11

(51) Int. Cl.
| | | |
|---|---|---|
| G01N 27/407 | (2006.01) | |
| G01N 27/00 | (2006.01) | |
| G01N 33/497 | (2006.01) | |
| C22C 5/04 | (2006.01) | |
| G01N 27/12 | (2006.01) | |
| G01N 33/00 | (2006.01) | |
| C22C 30/00 | (2006.01) | |

(Continued)

(52) U.S. Cl.
CPC ................. *C22C 5/04* (2013.01); *C22C 30/00* (2013.01); *C23C 14/14* (2013.01); *C23C 14/34* (2013.01); *G01N 27/125* (2013.01); *G01N 33/005* (2013.01)

(58) Field of Classification Search
CPC ......... C22C 5/04; C22C 30/00; C23C 14/14; C23C 14/34; G01N 27/125; G01N 33/005
See application file for complete search history.

(56) References Cited

U.S. PATENT DOCUMENTS 3,951,603 A * 4/1976 Obayashi ............... G01N 27/12
338/34
5,624,640 A * 4/1997 Potthast ................. G01N 27/12
204/432

(Continued)

OTHER PUBLICATIONS

K. Yvon et al., "LaMg$_2$PdH$_7$, a new complex metal hydride containing tetrahedral [PdH$_4$]$^{4-}$ anions", Journal of Alloys and Compounds 2007, pp. 34-38, vols. 446-447.

(Continued)

*Primary Examiner* — Lyle Alexander
*Assistant Examiner* — Robert Eom
(74) *Attorney, Agent, or Firm* — Sughrue Mion, PLLC

(57) ABSTRACT

Hydrogen sensor including a substrate on which there is deposited an active layer of material comprising a first element selected from the rare earth family, a second element selected from the platinum group metals and a third element selected from the alkaline earth metal family.

9 Claims, 3 Drawing Sheets

(51) Int. Cl.
*C23C 14/14* (2006.01)
*C23C 14/34* (2006.01)

(56) References Cited

U.S. PATENT DOCUMENTS 6,006,582 A * 12/1999 Bhandari ............. G01N 21/783
257/2
2004/0093928 A1 5/2004 DiMeo, Jr. et al.

OTHER PUBLICATIONS

K. Yvon et al., "Hydrogenation-Induced Insulating State in the Intermetallic Compound LaMg$_2$Ni", Physical Review Letters, Feb. 18, 2005, pp. 066043-1-066043-4, vol. 94, No. 6.
"Hydrogen Sensor", Wikipedia Entry, Dec. 24, 2008, XP002683065, http://en.wikipedia.org/wiki/Hydrogen_sensor.
International Search Report for PCT/EP2012/060755 dated Oct. 23, 2012.

* cited by examiner

HYDROGEN SENSOR WITH ACTIVE LAYER AND METHOD OF MANUFACTURING HYDROGEN SENSORS

CROSS REFERENCE TO RELATED APPLICATIONS

This is a National Phase Application in the United States of International Patent Application PCT/EP 2012/060755 filed Jun. 6, 2012, which claims priority on Swiss Patent Application No. 01191/11 of Jul. 15, 2011 The entire disclosures of the above patent applications are hereby incorporated by reference.

FIELD OF THE INVENTION

The present invention concerns a hydrogen sensor and a hydrogen detector integrating a sensor of this type, said detector allowing the detection of hydrogen and/or the measurement of concentration of hydrogen in a medium in which the sensor is arranged. The invention also concerns a method of manufacturing hydrogen sensors.

PRIOR ART

Known hydrogen detectors and sensors proposing pertinent features are expensive products to manufacture and consequently are of limited interest for use in mass markets. Solutions proposing less expensive technologies involve significant limitations in features, for example as regards the ranges of concentrations considered able to be measured and/or detected and/or the possibility of measuring or detecting hydrogen amongst several other gases, etc.

To overcome these various drawbacks, the invention provides different technical means.

SUMMARY OF THE INVENTION

Firstly, it is a first object of the invention to provide a hydrogen sensor and a detector integrating this type of sensor which have advantageous cost prices compared to existing hydrogen sensors and detectors.

It is another object of the invention to provide a hydrogen sensor and detector for measuring and detecting concentrations of hydrogen within a range of concentrations from 0 to 100% $H_2$.

Yet another object of the invention consists in providing a hydrogen sensor and detector which are accurate and reliable.

Finally, yet another object of the invention consists in providing a sensor and a detector for measuring and detecting the presence of hydrogen among a mixture of other gases.

The invention therefore concerns a hydrogen sensor including a substrate on which there is deposited an active layer of material including a first element selected from the rare earth family or a combination of at least two elements from the rare earth family, a second element selected from the platinum group metals (PGMs) or a combination of at least two elements from the platinum group metals (PGMs) (or combinations of the latter elements), and a third element selected from the alkaline earth metal family or a combination of at least two elements from the alkaline earth metal family.

The electrical resistance of the active layer changes in a substantially proportional manner to the concentration of hydrogen in contact with this active layer, which makes it possible to use this layer as a hydrogen sensor. Further, the electrical resistance of the active layer mainly depends on the partial hydrogen pressure and not on the total gas pressure of the medium in which the sensor is arranged. Moreover, the reaction on the active layer is reversible and the active layer remains intact even after several cycles of hydrogen absorption and desorption. The active layers are usable and effective over a vast range of hydrogen concentrations at the ambient temperature.

The response of the sensors is very rapid and signal reproducibility is good. The use of a metal compound such as $LaMg_2Pd$ can produce an active layer usable as a sensor. In a variant, the active layers are used for the purpose of measuring hydrogen.

Measurements have demonstrated that a hydrogen-induced insulating-metal transition occurs at substantially ambient temperature and at substantially low hydrogen pressures, between a phase partially charged with the $LaMg_2PdH_3$ composition and a phase entirely charged with the $LaMg_2PdH_7$ composition.

The first element of the active layer is preferably selected from the lanthanide family. Even more preferably, the first element of the active layer is selected from the sub-group including lanthanum, cerium, praseodymium, neodymium, samarium, europium or a combination of at least two metal elements from this sub-group.

Preferably, the second element of the active layer is selected from among palladium and platinum.

Preferably, the third element of the active layer is selected from among magnesium and calcium. Even more preferably, the third element of the active layer is formed of magnesium.

The active layer has a thickness of 1 nm to 0.1 mm and more preferably from 5 nm to 10,000 nm and even more preferably from 50 nm to 1,500 nm.

Advantageously, the substrate includes a material selected from among strontium titanate ($SrTiO_3$), glass (borosilicate), silicon and mica. Of course any other material suitable for the deposition of an active metallic layer using conventional vacuum deposition methods may be envisaged as the substrate.

In an advantageous embodiment, the active layer is coated with a coating layer, formed of palladium and/or platinum.

According to another aspect, the invention concerns a hydrogen detector including a hydrogen sensor and an electronic measuring module connected to said sensor, said electronic module being arranged to measure a state parameter of said sensor and being capable of delivering at output an electrical measurement signal representative of a concentration of hydrogen in a medium in which the sensor is arranged, characterized in that said hydrogen sensor is a hydrogen sensor including a substrate on which there is deposited an active layer of material including a first element selected from the rare earth family, or a combination of at least two elements from the rare earth family, a second element selected from the platinum group metals (PGMs), or a combination of at least two elements from the platinum group metals (PGMs) (or combinations thereof), and a third element selected from the alkaline earth metal family or a combination of at least two elements from the alkaline earth metal family.

According to an advantageous feature of the detector, the electronic measuring module is arranged to measure the electrical resistance of the active layer and to deliver a signal representative of said electrical resistance for example to a processing system or a storage system, and then to a display device.

According to a particular embodiment of the hydrogen detector according to the invention, the electronic measuring module further includes a comparator connected to said sensor, and the electrical measurement signal representative of the hydrogen concentration measured by the module from said sensor is delivered at the input of said comparator, said comparator being arranged to deliver at output a detection signal which is a function of the comparison of said input signal to at least one predetermined threshold signal and preferably, the electronic measuring module is arranged so that the at least one predetermined threshold signal is programmable.

The invention further provides a method of manufacturing hydrogen sensors, comprising the following steps:
- taking a substrate suitable for the application of an active metallic layer;
- depositing an active metallic layer on said substrate, the active metallic layer being form of a material whose first element is selected from the rare earth family, or a combination of at least two elements from the rare earth family, a second element is selected from the platinum group metals (PGMs), or a combination of at least two elements from the platinum group metals (PGMs), and a third element is selected from the alkaline earth metal family or a combination of at least two elements from the alkaline earth metal family.

The method used is particularly simple to implement and therefore inexpensive, offers good reproducibility, and can be carried out in a compact facility.

The active layer deposition is advantageously performed using a physical vapour phase deposition method (PVD) and preferably by cathodic sputtering. In this latter case, the cathodic sputtering atmosphere is mainly formed of argon. Again in the case of cathodic sputtering, prior to deposition, the substrate is heated to a temperature of at least 250° C., and preferably to a temperature of 300° C.

In an alternative embodiment, the active layer deposition is performed by vacuum evaporation.

The invention also concerns the use of a compound selected from among the following compounds: $LaMg_2Pd$, $LaMg_2Pt$, $Sc_{(x)}La_{(1-x)}(Mg_2Pd$, $La(1-x)Ce(x)Mg2Pd$, $LaMg(2-x)Ca(x)Pd$, $LaMg2Pd(1-x)Pt(x)$, $0<x<1$ to produce an active layer for a hydrogen sensor for evaluating the presence or concentration of hydrogen in contact with said active layer. Preferably, the $LaMg_2Pd$ will be used to form an active layer for a hydrogen sensor for evaluating the presence or concentration of hydrogen in contact with said active layer. The invention also concerns the use of an aforementioned compound, wherein said active layer, with the hydrogen of the medium into which said sensor is inserted, forms a hydride of variable composition according to the concentration of hydrogen in said medium, each particular composition of said hydride corresponding to a particular value of the electrical resistance of said active layer.

DESCRIPTION OF THE DRAWINGS

Other features and advantages of the hydrogen sensor and detector of the invention will also appear in the following detailed description of embodiments of the sensor and detector of the invention, this description being made with reference to the annexed Figures, given by way of non-limiting example and in which.

DETAILED DESCRIPTION OF THE INVENTION

"Platinum group metals" (PGM) means: ruthenium, rhodium, osmium, iridium, platinum, rhenium, palladium, or a combination of these elements.

"Alkaline earth metals" means: magnesium, calcium, strontium, barium, or a combination of these elements.

Rare earth metals means: lanthanum, cerium, praseodymium, neodymium, samarium, europium, gadolinium, terbium, dysprosium, holmium, erbium, thulium, ytterbium, lutetium or a combination of these elements.

Figure 3A:
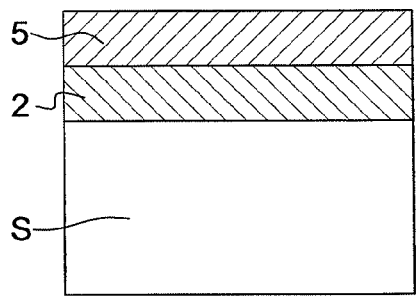
FIG. 3a is a schematic cross-section of a hydrogen sensor according to the invention.
Figure 3B:
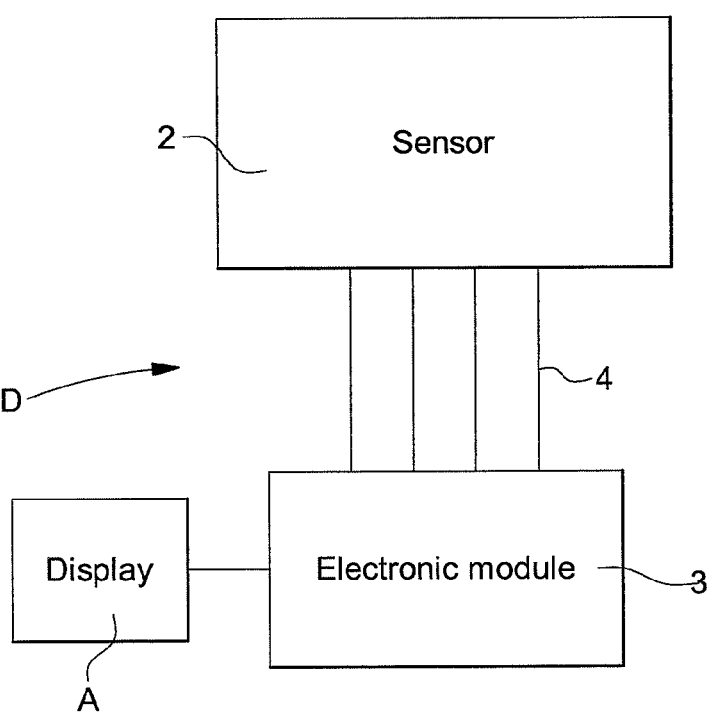
FIG. 3b is a diagram of an embodiment of a hydrogen detector incorporating a hydrogen sensor according to the invention.

FIG. 3a shows an example of a sensor 1 according to the invention. It includes a substrate S, for example in the form of a film having, for example, a thickness of 100 microns, on which a thin active layer 2 has been deposited. Sensor 1 is connected via its layer 2 to an electronic module 3 arranged to measure a state parameter of the sensor, in this case the electrical resistance of layer 2, via four (or two in a variant) electrical connections 4 to form a detector D shown in FIG. 3b. In an alternative embodiment, electronic module 3 and substrate S are integrated to form a single element. Module 3 is devised to measure the electrical resistance of the active layer, for example by the four point method or by any other suitable method and to deliver a measurement signal representative of the hydrogen concentration in the medium in which the sensor is placed. This measurement signal is processed by an electronic circuit and the measured concentration value is then displayed on a display screen A.

According to an alternative embodiment, the electronic measuring module 3 may be arranged to deliver a signal detecting the presence of hydrogen. In that case, the electronic measuring module further includes a comparator (not shown) and the electronic measurement signal representative of a hydrogen concentration measured by the electronic measuring module from said sensor is delivered at input to the comparator, the latter being arranged to deliver a detection signal as a function of the comparison of said input signal with at least one predetermined threshold signal. The electronic module is advantageously arranged so that the at least one predetermined threshold signal is programmable to one or more measured hydrogen concentration levels. According to requirements, the circuit could be arranged to deliver an alarm signal, for example an acoustic or visual signal, if one or more predetermined concentration thresholds are exceeded.

Active layer 2 is formed of a material comprising three elements: a first element is selected from the rare earth family or a combination of at least two elements from the rare earth family, a second element is selected from the platinum group metals (PGM) or a combination of at least two elements from the platinum group metals (PGM) and a third element is selected from the alkaline earth metal family or a combination of at least two elements from the alkaline earth metal family.

A few non-limiting examples of hydrogen sensitive active layers are given below: $LaMg_2Pd$, $LaMg_2Pt$, $Sc_{(x)}La_{(1-x)}Mg_2Pd$, $La(1-x)Ce(x)Mg2Pd$, $LaMg(2-x)Ca(x)Pd$, $LaMg2Pd(1-x)Pt(x)$, $0<x<1$, etc.

Various types of substrates may be used, such as for example a substrate formed of strontium titanate ($SrTiO_3$), glass (borosilicate), silicon, mica or other elements provided that they are suitable for the active layer deposition using conventional vacuum deposition methods.

The thickness range of active layer 2 is preferably: 1 nm to 0.1 mm and more particularly from 5 nm to 10,000 nm and even more particularly from 50 nm to 1,500 nm. For the substrate, in principle there is no limitation as to thickness. In practice, it is useful to consider a minimum thickness of 1 micron.

A particularly advantageous method is provided for producing active layer 2. Thus, a thin layer is deposited by physical vapour deposition (PVD) for example by cathodic sputtering or by evaporation or another type of physical vapour deposition. It will be noted that CVD or ALD or ionic implantation depositions may also be envisaged.

According to an example embodiment, a suitable substrate for depositing the thin metallic layer 2, such as for example a $SrTiO_3$ substrate, is heated to 300° C. and is placed in an argon atmosphere at a pressure of $10^{-4}$ bars.

An active layer of around 120 nm is obtained after several minutes using a sputtering end-piece having a power of 10 watts. No heat treatment is required to treat the layer thereby obtained.

The active layers thereby produced are then pre-charged with hydrogen. To achieve this, the sensor is placed in a medium containing hydrogen until the active layer is saturated in $H_2$.

Figure 1:
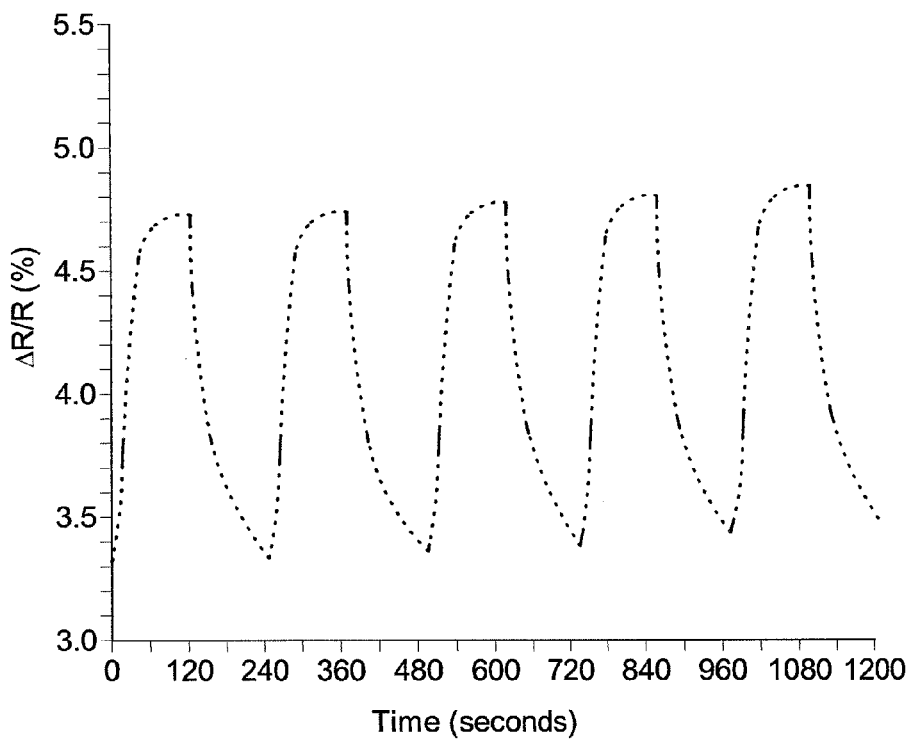
FIG. 1 is a graph showing the evolution of relative electrical resistance with time for a sensor of the invention subjected to a series of pure hydrogen absorption and desorption cycles at ambient temperature (25° C.).

The graphs in FIGS. 1 and 2 were produced from a $LaMg_2Pd$ ternary alloy. This active layer must be precharged with hydrogen to attain the $LaMg_2PdH_3$ hydride, prior to use as a hydrogen sensor according to the invention.

FIG. 1 shows an example substrate with a precharged active layer subjected to a series of pure hydrogen absorption and desorption cycles at ambient temperature (25° C.). The electrical resistance of the active layer is measured by a known measuring method, in this case the four point method. The value R is the electrical resistance of the $LaMg_2PdH_3$ alloy (composition of the active layer in the absence of hydrogen). The cycles are based on an increase in pressure up to 1 bar for 2 minutes and a decrease in pressure to a vacuum for 2 minutes, as shown in the Figure. Thus, at time t=0, 1 bar of hydrogen is introduced into the sensor chamber (vacuum), at t=2 minutes, the chamber is evacuated again, at t=4 minutes, 1 bar of hydrogen is reintroduced, etc. It is observed that the electrical resistance increases around 1.5% during absorption phases and decreases by a similar value during desorption. The active layer produced permits a rapid response and good signal reproducibility. On a scale of several minutes, the drift is substantially low, whereas on a scale of several hours the drift is substantially zero. Analyses from profiles obtained using X rays before and after hydrogenation have confirmed the presence of the active $LaMg_2Pd$ phase, the intermediate partially charged $LaMg_2PdH_3$ phase, the entirely charged $LaMg_2PdH_7$ and lanthanum oxide $La_2O_3$ phase.

Figure 2A:
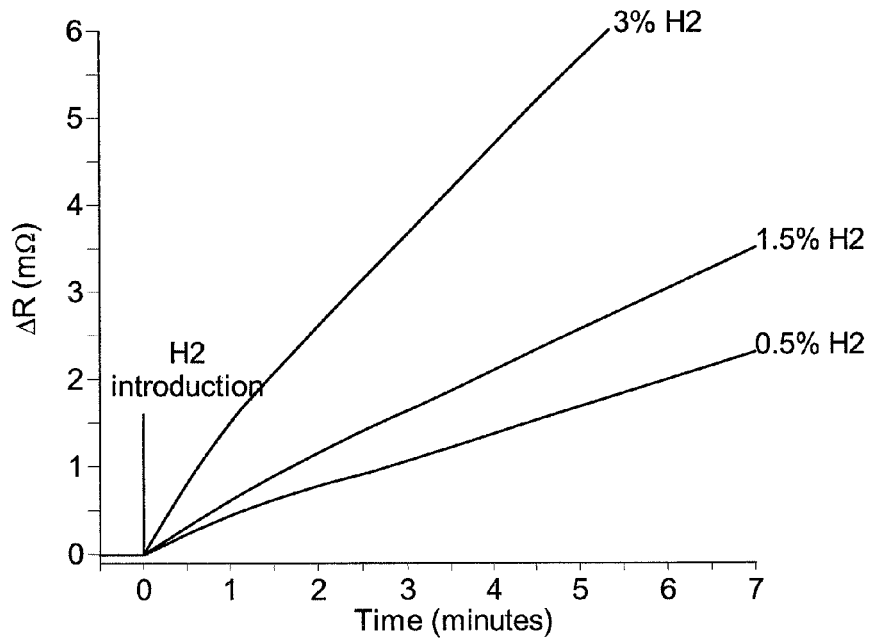
FIG. 2a is a graph showing the evolution of absolute electrical resistance with time for a sensor of the invention for three example hydrogen concentrations.

FIG. 2a illustrates measurements performed with an active layer 2 subjected to various hydrogen concentrations (0.5%, 1.5% and 3%) added to the argon atmosphere. FIG. 2a shows that the electrical resistance increases immediately for all concentrations. It should be noted that the lowest concentration (0.5%) satisfies the requirements of an easily identifiable signal, for producing a low hydrogen concentration sensor. The Applicant observed that the active layer did not present any signal degradation over extended cycles.

Figure 2B:
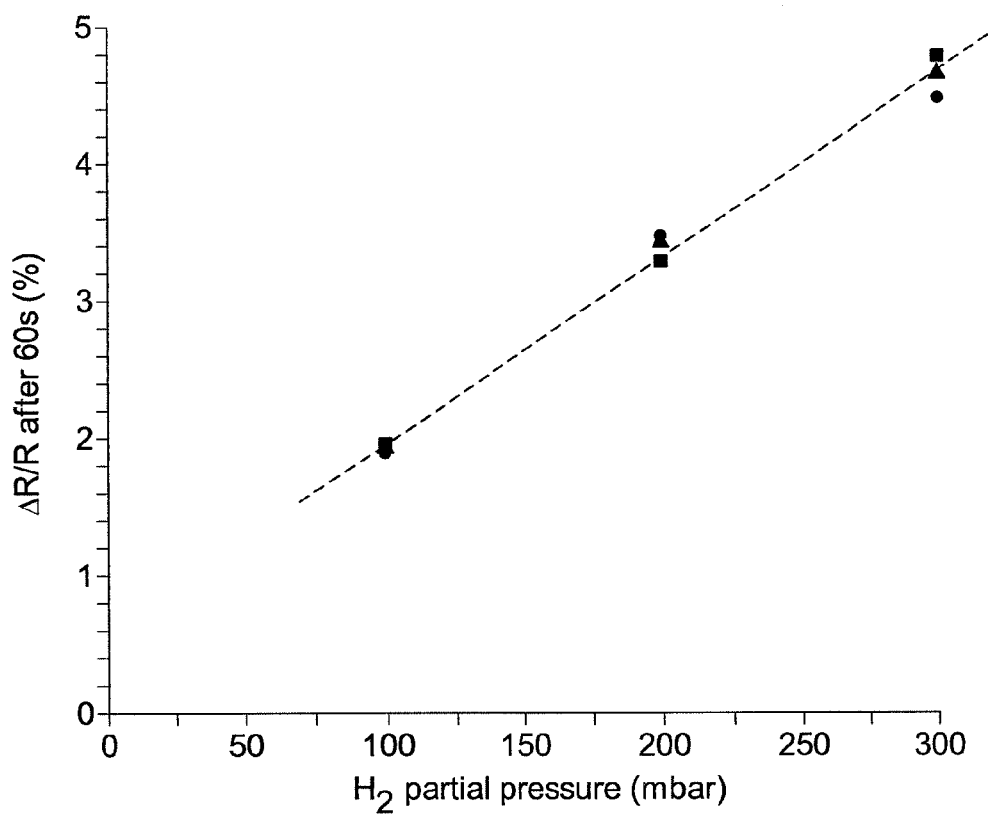
FIG. 2b is a graph showing the evolution of relative electrical resistance for a sensor of the invention subjected to partial hydrogen pressures of up to 300 mbar and partial argon pressures of between 700 and 900 mbar.

FIG. 2b illustrates the results of measurements performed using three sensors of the invention, with partial pressures of up to 300 mbar of hydrogen and partial argon pressures of between 700 and 900 mbar. FIG. 2b shows the relative electrical resistance variation (in % after 60 seconds) for an active layer of $LaMg_3Pd$ on three distinct substrates (respectively symbolised by squares, triangles and circles in FIG. 2b), for partial pressure varying between 100 and 300 mbar, the rest of the mixture being formed of argon, for a total pressure of 1 bar. It is observed that the relative electrical resistance increases regularly and significantly with excellent reproducibility. The sensor can therefore provide partial hydrogen pressure values in a reliable and accurate manner, even for concentrations as large as 20% or 30% hydrogen. Further, tests conducted with air instead of argon produced similar results.

If hydrogen is present in the atmosphere, the hydrogen is absorbed by active layer 2. This absorption corresponds to a conversion reaction of $LaMg_2PdH_3$ into $LaMg_2PdH_7$. Since these two hydrides have different electrical resistivity, the measured electrical resistance depends on the level of $LaMg_2PdH_3$ converted into $LaMg_2PdH_7$, which in turn depends on the concentration of hydrogen.

Variant with a Coating Layer

According to this first embodiment, with high hydrogen concentrations, once all of the $LaMg_2PdH_3$ has been converted into $LaMg_2PdH_7$, the sensor is saturated and the electrical resistance of the active layer no longer increases with the hydrogen concentration. In these high hydrogen concentration cases, the device is no longer capable of performing a measuring function and is limited to a detection function.

To overcome this drawback, the active layer 2 (for example a layer of $LaMg_2Pd$) is coated with a thin layer 5 (FIG. 3b), typically around 4 nm, of palladium and/or platinum. With this coating layer 5, the active layer reacts differently. Indeed, instead of the conversion reaction described above, this assembly results in a new equilibrium between the hydrogen content x in the active layer, here the $LaMg_2PdH_x$ hydride, and the hydrogen pressure. Owing to this equilibrium, the sensor does not reach complete saturation, but demonstrates more rapid kinetics and a shorter recovery time. The field of application is thus extended from the detector to sensors. In an alternative embodiment, the palladium layer is replaced by a similar layer of a Pt and Pd alloy, possibly with nickel.

The difference in reactivity according to hydrogen pressure may be explained by the capacity of palladium to dissociate the $H_2$ hydrogen molecule into monoatomic hydrogen which is much more reactive. This effect also explains another very positive aspect of the palladium layer. When oxygen is present in the atmosphere, the hydrogen is much more quickly reabsorbed from the layer, because monoatomic hydrogen reacts on the palladium surface to form water or molecular hydrogen. The sensor response time when the hydrogen concentration drops is thus greatly improved.

The invention claimed is:

1. A hydrogen sensor including:

a substrate; and an active layer of a material formed on the substrate, the material comprising:

a first element which is an element from the rare earth family or a combination of at least two elements from the rare earth family, a second element which is an element from the platinum group metals or a combination of at least two elements from the platinum group metals, and a third element which is an element from the alkaline earth metal family or a combination of at least two elements from the alkaline earth metal family, wherein the active layer has property of absorption and desorption of hydrogen at ambient temperature, and wherein the active layer comprises a material selected from a group consisting of:

$LaMg_2Pt$, $Sc_{(X)}La_{(1-X)}Mg_2Pd$, where X is a numerical value greater than 0 and less than 1, $La_{(1-Y)}Ce_{(Y)}Mg_2Pd$, where Y is a numerical value greater than 0 and less than 1, $LaMg_{(2-Z)}Ca_{(Z)}Pd$, where Z is a numerical value greater than 0 and less than 1, and $LaMg_2Pd_{(1-W)}Pt_{(W)}$, where W is a numerical value greater than 0 and less than 1.

2. The hydrogen sensor according to claim 1, wherein the active layer has a thickness of 1 nm to 0.1 mm.

3. The hydrogen sensor according to claim 1, wherein the substrate includes a material selected from among strontium titanate, glass, silicon and mica.

4. The hydrogen sensor according to claim 1, wherein the active layer is coated with a coating layer consisting of platinum or an alloy of palladium and platinum.

5. The hydrogen sensor according to claim 1, wherein the active layer comprises $LaMg_2Pt$.

6. The hydrogen sensor according to claim 1, wherein the active layer comprises $Sc_{(X)}La_{(1-X)}Mg_2Pd$, where X is a numerical value greater than 0 and less than 1.

7. The hydrogen sensor according to claim 1, wherein the active layer comprises $La_{(1-Y)}Ce_{(Y)}Mg_2Pd$, where Y is a numerical value greater than 0 and less than 1.

8. The hydrogen sensor according to claim 1, wherein the active layer comprises $LaMg_{(2-Z)}Ca_{(Z)}Pd$, where Z is a numerical value greater than 0 and less than 1.

9. The hydrogen sensor according to claim 1, wherein the active layer comprises $LaMg_2Pd_{(1-W)}Pt_{(W)}$, where W is a numerical value greater than 0 and less than 1.

* * * * *